(12) United States Patent
Iger et al.

(10) Patent No.: US 6,206,843 B1
(45) Date of Patent: Mar. 27, 2001

(54) ULTRASOUND SYSTEM AND METHODS UTILIZING SAME

(75) Inventors: Yoni Iger, Haifa; David Shalhevet, Kefar Veradim; Dmitry Elman, Maalot; Emanuel Segal, Haifa; Salah Hassoon, Shefaram, all of (IL)

(73) Assignee: Ultra Cure Ltd., Nesher (IL)

( * ) Notice: Subject to any disclaimer, the term of this patent is extended or adjusted under 35 U.S.C. 154(b) by 0 days.

(21) Appl. No.: 09/239,153

(22) Filed: Jan. 28, 1999

(51) Int. Cl.[7] ................................................ A61B 17/22
(52) U.S. Cl. ................................................ 601/2
(58) Field of Search ............................. 600/437, 439, 600/472, 369; 601/2

(56) References Cited

U.S. PATENT DOCUMENTS

| | | | |
|---|---|---|---|
| 4,294,119 | * 10/1981 | Soldner | 73/625 |
| 4,434,799 | * 3/1984 | Taenzer . | |
| 5,882,302 | * 3/1999 | Driscoll | 600/371 |

FOREIGN PATENT DOCUMENTS

| | | |
|---|---|---|
| 29 02 331 | 7/1980 | (DE) . |
| 0 112 082 | 6/1984 | (EP) . |
| WO98/32379 | 7/1998 | (WO) . |
| 9832379 | * 7/1998 | (WO) . |

OTHER PUBLICATIONS

Hynynen et al., "The effect of various physical parameters on the size and shape of necrosed tissue volume during ultrasound surgery", *Acoust. Soc. Am.*, 95:1541–1549, (1994).*

Hynynen et al., "Focused Ultrasound Surgery Guided by MRI", *Science & Medicine*, 62–71 (1996).*

* cited by examiner

*Primary Examiner*—Marvin M. Lateef
*Assistant Examiner*—Eleni Mantis Mercader
(74) *Attorney, Agent, or Firm*—Browdy and Neimark, P.L.L.C.

(57) ABSTRACT

The present invention concerns an ultrasound system for the production of an acoustic wave pressure on a desired organ. The present invention further concerns a method for closing a liquid containing vessel, such as a blood vessel, by applying a first pulse of acoustic pressure for emptying the vessel of liquid, and than applying a second pulse for adhering the walls of the vessel to each other.

20 Claims, 4 Drawing Sheets

ULTRASOUND SYSTEM AND METHODS UTILIZING SAME

FIELD OF THE INVENTION

The present invention concerns an ultrasound system for the administration of ultrasound beams and methods for using this system both for therapeutical and/or cosmetic purposes.

BACKGROUND OF THE INVENTION

Ultrasound is a mechanical wave with a frequency above the audible range that propagates by motion of particles within the medium. The motion causes compressions and refraction of the particles so that a pressure wave travels along with mechanical disturbance.

Ultrasound has been used for several decades for diagnostic purposes, for visualizing soft tissues within the body of the patient. A system which utilizes ultrasound for diagnostic purposes, usually comprises a wave-generating transducer capable of generating an ultrasonic wave, and an ultrasonic receiving transducer capable of receiving the ultrasonic wave. Since the density of the tissue through which the ultrasound wave propagates, has an effect on the speed and attenuation of the wave, if the ultrasound wave passes through tissues having different densities, for example due to a presence of a tumor therein, the wave is distorted, which distortion can be monitored by the receiving transducer. Since ultrasound propagation through air is highly attenuated, the wave-generating transducer should be coupled to the body of the patient to be diagnosed through a specific coupling fluid medium, such as an ultrasonic gel.

U.S. Pat. No. 4,434,799 discloses an ultrasonic apparatus for medical examination wherein the patient organ to be diagnosed, for example a breast, is positioned between an ultrasonic wave-generating transducer and an ultrasonic receiving transducer. In contact with the skin, and at some distance from both the wave-generating transducer and the second receiving transducer, are first and second ultrasonic windows, respectively. The system contains two guiding devices containing a fluid medium, one for guiding ultrasonic waves from the transducer to the first window and from there to the body of the patient, and one for guiding the ultrasonic waves from the body of the patient to the second ultrasonic window and from there to the receiving transducer. This diagnostic apparatus, which emits a non-focused ultrasound wave, enables guiding of the ultrasound wave trough a liquid medium, and eliminates the need to use a coupling gel on the body of the patient, or the need to immerse the body of the patient to be examined in a water tank.

Ultrasound has also been proposed for therapeutical purposes, used in the area of physiotherapy, cardiology, ophthalmology, cancer therapy, and dentistry, Non-focused waves are used, for example, in physiotherapy and focused ultrasonic beams are used for selectively destroying a living tissue in a desired location, for example, for destroying a malignant tissue. Many times, destruction by a focused ultrasound beam is combined with diagnostic ultrasound imaging which locates precisely the region of the tissue to be destroyed. Several clinical trials for the treatment of benign and malignant tumors of the prostate, bladder, kidney and eye have been conducted by using this method.

Another therapeutical application of the ultrasound, is its use to disintegrate kidney stones where the ultrasound high energy pulses produced by a lithotripter are absorbed in the condensed stone. The stone is slowly broken into small fragments by the energy forces, and is simultaneously monitored by X-ray vision or ultrasound vision. The ultrasound application continues until the broken stone fragments are small enough to be washed through the urinary tract. In practice, the body of the patient, or at least the area containing the organs to be treated, is immersed during the ultrasound administration phase in a water tank.

Ultrasound beams can be focused by using self-focusing radiators or special transducers, lenses or reflectors, or by electrical focusing.

As the ultrasound wave propagates through tissues, part of the energy is absorbed and converted to thermal energy. The thermal elevation of the tissue caused by energy absorption is inversely proportional to the beamed area. The greatest temperature elevation is induced at the focus of the beam, termed "the focal point" where it can be several hundred times more than the overlying tissue. This allows tissue at the focal point to be selectively destroyed while temperature elevation of the surrounding tissue is negligible.

Sharp focusing also allows fast energy delivery so that temperature levels that cause proteins to coagulate and cells to die can be reached in only a few seconds or second parts. The short exposure to sharply focus beams produces sharp temperature gradients and the transition distance between the coagulated cells and damaged cells may be only a few cells wide.

Ultrasound irradiation, where the focal point was at the blood vessel, was demonstrated in vivo to be able to occlude blood vessels and coagulate capillaries and larger arteries. Non-invasive treatment using focused ultrasound is being hindered by the fact that in order for the ultrasound wave to propagate the treated organs of the patient's body has to be immersed in a water tank, which is extremely cumbersome, especially where the patient is handicapped or elderly. Such immersion is almost impossible in cases where the treated area is the face. Even where immersion of the patient's body in a water bank is feasible, it hinders the manipulation of the focused ultrasound beam.

Another concept for solving the problems of the coupling liquid medium placed between the ultrasound transducer and the patient is achieved by immersing the whole ultrasound system within a water tank (Kullervo Hynynen, Science and Medicine, September/October 1996, pp 62–271). This arrangement is also quite cumbersome, not enabling free manipulation of the system.

WO 98/32379 discloses an ultrasonic system capable of providing a focused ultrasonic beam comprising a container holding a liquid medium. The container guides the ultrasonic beam from the ultrasonic generating element to the desired location of administration. The focal point of the focused ultrasonic beam according to WO 98/32379 is always outside of the container, as it is defined that the length of the container is smaller than the ultrasonic focal beam's length. According to this publication the focal point of the ultrasonic beam either immediately outside of the container, and in that case the beam is used to destroy biological tissue on the skin of the treated individual or, alternatively, the ultrasonic focal point may be some distance from the end of the container, and thus destruction of biological tissue is carried out at a desired depth of the body of the treated individual.

At times it is desired to provide pressure on a liquid holding organ such as a blood vessel, a gland a tube, without causing damage to the walls or membranes of the organ. For example it is desired at times to apply pressure on damaged blood vessels in order to stop them from external or internal bleeding; it is desired to apply pressure on gland or ducts, such as saliva, sweat and tear glands, in order to eliminate the excessive secretion therefrom; it is desired to empty and close tubes of the reproducing tract delivering sperm or ova in order to cause reversible sterilization; it is desired to empty blood vessels of their contents prior to their closure by application of energy in order to reduce the heat transport cooling effect of blood. To date, usually the pressure applied to those vessels, tubes or glands, is carried out by applying a mechanical pressure, for example, with the aid of forceps, on the tubes, glands or vessels. Such externally applied mechanical pressure, may not always be precise and controlled, and at times may cause damage such as tearing to the walls of the vessel, furthermore such pressure can not be applied to tissues that are located deeper within the body.

It would be highly desirable to provide a system and method to produce controlled pressure on liquid holding or liquid transferring organs such as vessels, glands, tubes, which pressure would not harm or damage the walls of such organs.

SUMMARY OF THE INVENTION

The present invention concerns an ultrasonic system for the creation of a controlled acoustic pressure on an organ for example for emptying a blood vessel or stopping leakage from an injured blood vessel. As in WO 98/32379, rather than immersing the treated patient in a liquid tank, or rather than immersing the whole ultrasound system in a liquid filled container, the ultrasound generating element is coupled to a container holding a liquid medium. The focal point of the ultrasonic beam is created inside the container, and as a result an acoustic pressure wave propagates from the container in the direction of the advance of the beam.

The acoustic pressure wave can then be used to apply pressure on the organ for example to push liquid such as blood, sperm, saliva, sweat or tears out of vessels, tubes, glands or ducts, without damaging the walls of the vessel, tube or gland, or alternatively can prevent leakage of liquid from said organ, the precise mode of activity depends on the location of administration of the pressure.

Thus, the present invention provides an ultrasound system for the creation of an acoustic pressure wave for providing pressure on an organ comprising:

(i) at least one ultrasound generating element capable of producing a focused ultrasound beam; and (ii) at least one container holding a liquid medium coupled at one end to the ultrasound generating element for permitting propagation of the focused ultrasonic beam from the ultrasound generating element to the desired location of the organ, said container having a width such that the ultrasound beam propagates therein without bouncing on the side walls of the container; and a length such that the beam's focal point is within the container The acoustic pressure wave is intended to provide pressure on an organ, in particular a liquid containing organ such as a vessel, gland or tube, typically for emptying the organ from said liquid or for stopping leakage of liquid therefrom. This can be carried out, for example, for creating a local pressure on a open or injured blood vessel, in order to cause cessation of local, internal or external bleeding. The pressure may also be applied on liquid containing glands, such as salvia glands, sweat glands and tear glands, in order to emit excessive secretion therefrom. The pressure may also be applied on tubes of the reproductive tract, which delivers sperm or oocytes, respectively, in order to cause their closure, for sterilization purposes. Sterilization by gentle application of pressure, which causes the inner walls of the tubes to adhere to each other is usually reversible, as the pressure applied is controlled and no damage is caused to the walls of the tubes. Sterilization is than carried out by ablation of the duct for example by administration of a focused ultrasonic pulse of a high intensity. If sterization is to be reversed the duct can be re-opened by using ultrasound energy or by surgery. Thus the system of the invention may be used at times to close organs such as tubes.

The controlled pressure may be applied for causing abortion by stopping the blood supply (due to application of pressure) to the developing embryo.

The pressure may also be applied to small blood vessels of the heart since at that particular location their transit or permanent closure encourages angiogenesis.

Another application of pressure may be to nerves or muscles in order to inhibit or stimulate transfer of electric pulses, as the case may be for example for decreasing pain, stimulating dysfunctional nerves or muscles and the like.

According to the preferred embodiment of the invention, the system is used as a system for pushing liquid out of treated blood vessels, which may be a capillary, a small vein or artery. By pushing the blood out of the blood vessel, the cooling capacity of the blood in the vessel is drastically reduced. Thus, the walls of the empty blood vessel may be fused to each other by ablation, produced by heat, either by application of a laser beam, or by application of focused ultrasonic beam, for example, according to teaching of WO 98/32379.

Thus, the present invention concerns a method for blocking a liquid containing vessel, at a desired portion thereof, in a treated subject, comprising the steps of:

i) applying on the vessel at said portion a first ultrasonic pulse to produce an acoustic pressure wave having parameters sufficient for pushing liquid out of the vessel at said desired portion substantially without damaging the walls of the vessel; and ii) within a time period before liquid returns to the emptied portion of the vessel, applying a second ultrasonic pulse, being a focused ultrasonic wave with an acoustic focal point a said portion, causing local elevation of temperature at said portion to adhere walls of the vessel at said portion with one another.

A method for blocking a liquid containing vessel, at a desired portion thereof, in a treated subject, comprising the steps of:

i) applying on the vessel at said portion a first ultrasonic pulse to produce an acoustic pressure wave having parameters sufficient for pushing liquid out of the vessel at said desired portion substantially without damaging the walls of the vessel; and iii) within a time period before liquid returns to the emptied portion of the vessel, applying a second ultrasonic pulse, being a focused ultrasonic wave with an acoustic focal point a said portion, causing local elevation of temperature at said portion to adhere walls of the vessel at said portion with one another.

The two-step method of the present invention may be carried out by using the above system of the invention, while adjusting the distance between the generating element, and the container, so that initially the focal point falls inside the container thus creating a pressure wave for emptying the liquid out of the vessel, and at the second step the distance is changed so that the focal point falls outside the container, in the blood vessel.

By the method of the present invention, initially the liquid containing vessel is emptied and then its walls are adhered to each other by the heat created at the focal point and the vessel is thus closed.

Preferably the liquid containing vessel is a blood vessel of a desired size. Examples of conditions where it is desired to empty and close blood vessels are: closure for cosmetic purposes for elimination of non desired blood vessel, such as capillaries, spider veins and the like; for medical purposes for closure of leaking internal veins after trauma or operation; for closure of blood veins leading to tumors in order to cur the blood supply of the tumor and thus lead to its destruction, for closure of blood veins of hemorrhoids and the like.

Typically, when carrying out the method of the invention the initial pulses, for emptying the vessel by acoustic pressure, is longer than the second pulse and has a lower intensity, sufficient to empty the vessel without causing its destruction. If the vessel for example a blood vessel, is wide, a single emptying pulse and ablating pulse may not be sufficient and it may be required to administer several cycles of alternating "empytying" and "ablating" pulses until the whole width of the vessel is covered.

The term "focused ultrasound beam" refers to an ultrasound beam which area is becoming progressively smaller and its intensity progressively higher as the beam is further away from the ultrasound generator, at the acoustic focal zone the area of the beam is smallest and the intensity the highest. The beam's area is equivalent to the near zone in a regular beam, where the beam runs in parallel before being dispersed.

The term "ultrasound generating element capable of producing a focused ultrasound beam" may refer to a signal generator, power amplifier, matching unit, a transducer which is capable of producing a focused beam or is to a complex of these elements which produce a regular, i.e. unfocused beam coupled to focusing mean such as self-focusing radiators, reflectors or lenses and the like.

Where the generating element does not include focusing means such as lenses, the focused beam is created by the transducer itself, for example, by constructing the transducer so that its irradiation zone has a certain curvature or by other means such as working at areas having maximal energy concentration along the beam.

The ultrasound generating element may alternatively comprise a regular transducer, i.e. having a straight irradiation zone, coupled to focusing means such as a self-focusing radiator, reflector or electrical focusing unit or lens capable of focusing the ultrasonic wave and thus creating the focused ultrasound beam. Preferably, the focusing means are acoustic lenses.

The lenses are typically high-density plastic lenses, of different curved diameters, which curve depends on the desired properties of beam to be produced. Preferably, the lenses are made of plexiglass. If desired, the system may comprise a plurality of lenses, of various curved dimensions, capable of detachably engaging with the transducer, in order to produce a wide variety of focused beams having varying, properties. Alternatively, instead of using a lens it is possible to use focused transducers (i.e. transducers that produce a focused ultrasonic beam).

The ultrasound generating element is coupled to a container holding a liquid medium capable of transmitting ultrasound waves, and the focal point is created inside the liquid medium, and as a result the focus falls within the coupling medium of the container. What goes out of the container is the region of the beam after the focal point that becomes progressively wider, thus having a low intensity which is not sufficient to cause ablation since this intensity is below the threshold of damage of biological tissues. However this intensity still has enough radiation force to push liquid of low pressure out of its vessel. Them after the focal point is wider affecting a larger area for example the entire blood vessel diameter. All these effects are in the direction of irradiation and propagation of the acoustic wave.

The container may be, a priori, filled with the acoustic coupling liquid medium or may be initially empty and filled with the appropriate liquid medium only immediately before the administration of the focused beam, to create the acoustic pressure wave. The acoustic coupling medium and the container itself can be also replaced by a solid horn-like unit, and the procedure is carried out in essentially the same way.

The liquid may be a degassed solution such as water, in order to reduce loss of the energy of the beam due to formation of cavitation bubbles.

Preferably, the container should have an essentially conical shape, in order to adapt to the general shape of the focused beam which is also conical.

The dimensions of the liquid holding container should be such as to accommodate the full width of the focused acoustic beam, i.e. that the container at each point is wider than the ultrasound beam at that point so as to so avoid "bouncing" of the beam on the walls of the container. Where a conic container is used, the width of the cone in its base and the angle of its slope should match, almost precisely, the dimensions of the acoustic beam in order to reduce to a minimum the turbulence of the liquid caused by the energy transducer. However, if the internal part of the beam-holding container has dimensions greater than the diameter of the beam at each point along the axis, it can be of different shapes. It is also possible that it least part of the inner space of the container is made of a whole solid material, and not aquatic solutions, albeit at the cost of higher energy losses.

F number, refers to the relation between r (curvature) of lens and d (diameter) of the transducer. Since the construction of the cone is preferably according to the shape of beam, it is preferable that irradiation is performed using rather small F numbers (1–5). Tie advantage of using small F numbers is that the heat loss is smaller since the beam passes through a smaller distance; the slope of beam is higher; so that the effects are more localized: and the distance of influence is shorter and undesired effects on surrounding tissues are reduced.

According to the invention, the length of the container should be such that the focal point of the acoustic beam is inside the distal (uncoupled) part of the container, i.e. the length of the container is larger than the length of the ultrasound beam from its point of origin to the focal point.

The container is preferably made from material which is a poor heat conductive material. For external usage, transparent material which enables better observation of the treated zone may be used or the distal end of the container may be attached to an optic fiber.

In accordance with a preferred embodiment of the invention, the distance between the cone and ultrasound generating element is adjustable, in order to change the location of the container in respect to the focal point. The change in the position of the transducer in respect to the container enables the utilization different zones of the acoustic beam for different purposes.

Preferably, the system may comprise a plurality of containers, of various sizes, each one capable of detachably engaging with the ultrasound generating element, in order to accommodate for the various dimensions of the beams. Alternatively, the cone can be composed of a flexible material which can be modulated (elongated or shortened) according to the varying beam sizes. By another alternative, the distance between the container and the ultrasonic generating element is adjustable.

According to the most preferred embodiment of the invention, the system comprises three varying elements in combination:

a series of acoustic lenses of different curve dimensions, capable of detachably engaging with the other components of the ultrasound generating element, typically with the transducer in order to provide a plurality of focused beams of varying sizes and focal depths;

means for varying the distance between the ultrasound generating element and the coupled guiding container holding the liquid medium;

a plurality of liquid-holding containers capable of detachably engaging either with the ultrasound generating element in order to accommodate for the varying beam sizes and focal depths.

As can be seen, the depth of the focal point may be changed either by changing the ultrasound generating element (for example by changing the lens, or using curved transducers with different curvatures); or the distances between the container and the ultrasound generating element or the frequency. The size of the liquid holding container may be changed in order to accommodate the different depths of the focal point.

By changing the precise position of the focal point inside the container, it is possible to control the physical properties of the acoustic pressure wave. Where the system of the invention is used to empty the liquid containing vessels, as an emptying, step, before an ablation step of fusing the walls of the vessels together, the same system may be used. In the first "emptying" step the focal point will fall inside the container, which will cause acoustic pressure on the liquid containing vessel and will push the liquid out of the vessel at the point of application. As a second "ablating" step, the focal point of the acoustic wave will be created directly on the vessel, which will cause, due to thermal alleviation, fusion of the walls of the vessels to each other and thus their closure.

The focal point may be determined theoretically by utilizing the following formula (Gordon S. K. 1990 Acoustic Waves: devices, imaging and analog signal processing. Prentice Hall Inc. Englewood Cliffs, N.J. pp 652).

$$F(\text{Focal point}) = \frac{r}{(1 - 1/n)}$$

r=curvature of lens
n=Cp/Cw
Cp=speed of sound in the material from which the lenses are made (for example in plexiglass 2.7 mm/hr)
CW=speed of sound in the liquid medium (for example in water at 20° C. 1.48 km/hr)

Other physical methods for determining the focal zone are well known in the art and may be used in addition or instead of the method outlined above.

The slope of the inner part of the container e.g. a cone should be such that at any distance along the beam, it is fully engulfed by the cone. Preferably, the inner diameter of the cone is about 1 mm greater than the outer diameter of the ultrasound beam engulfed thereon at the same point, Damianou C. and Hynynen K, J. Acoust. Soc. Am. 95 1641–1649 (1993)].

The system of the invention can be composed of advanced and flexible materials, enabling change of the lens curvature and therefore the focal length, without replacing the lens themselves. Such a construction enables the same container to form narrow or wide openings at its distal part, enabling transfer of narrow or wide beams therethrough, this can save the use of many replaceable containers of different openings and sizes. The above two elements can be concomitantly operated, using a particular threading applying force on both flexible lens and the container to change their dimensions, enabling to change focal length and its location during irradiation.

The invention will now be further elaborated with reference to some non-limiting drawings and examples.

DETAILED DESCRIPTION OF THE INVENTION

Figure 1:
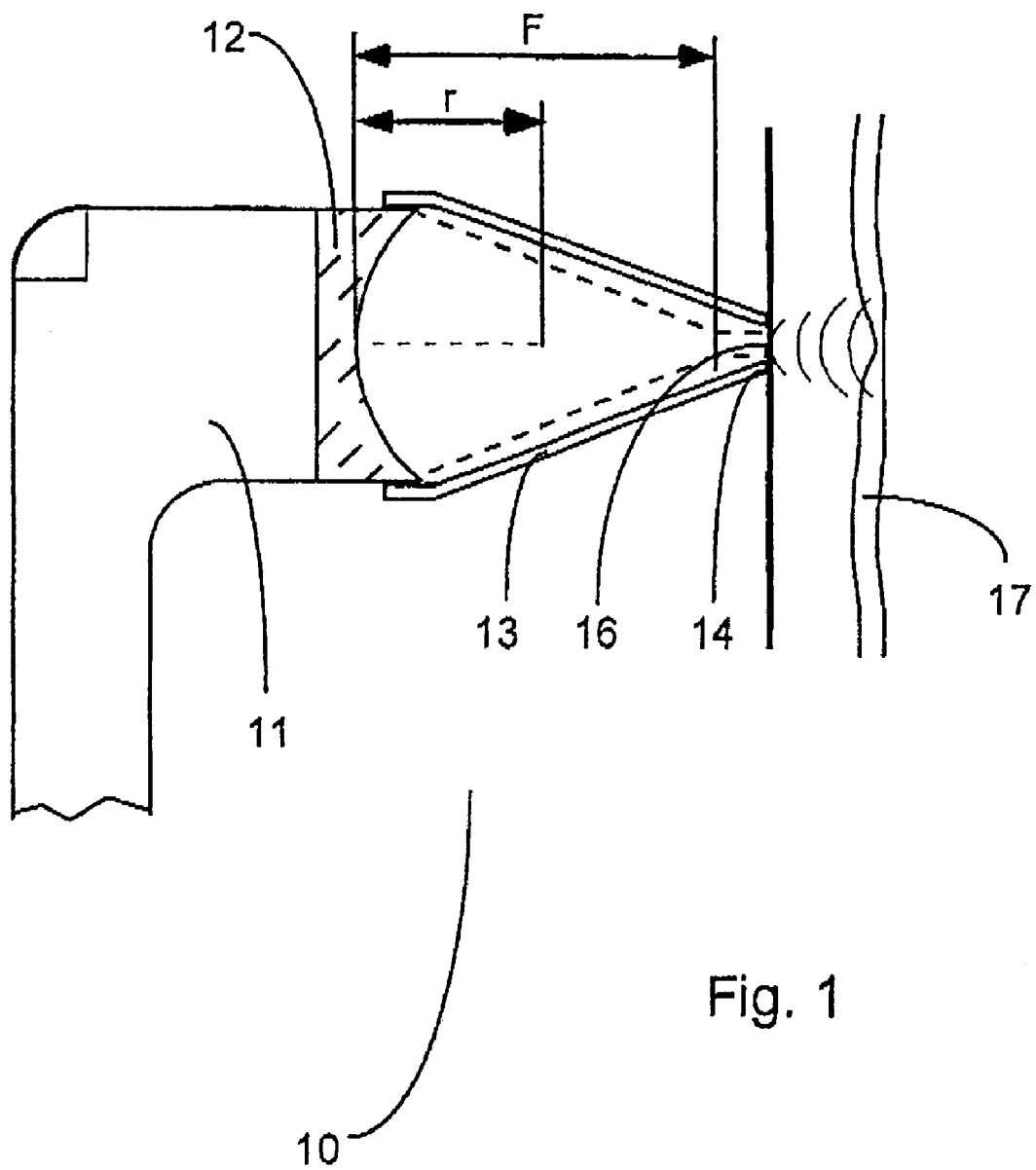
FIG. 1 shows a planar view of an ultrasound system in accordance with the invention.

The ultrasound system 10 of the invention is shown schematically in FIG. 1. This system is suitable for administration of an acoustic pressure wave to any liquid containing organ such as a blood vessel, gland, tube etc. The system comprises a signal generator coupled to an amplifier and matching unit (not shown) and an ultrasonic transducer 11, coupled directly or via an acoustic fiber, to an acoustic lens 12 made of plexiglass, having a curvature r. The length of the beam to the focal point is designated as F. Preferably, the coupling is a detachable attachment, for example by constructing the uncurved side of the lens to be engraved so it has a step that exactly fits the transducer (not shown). By pressing the step towards the transducer the lens and transducer are attached to each sad by application of force they can be detached, which construction enables detaching a lens having a specific curve dimension from the transducer and replacing it by another lens of a different curve dimension in order to change the length of the focal point F.

The container 13 is attached to the rims of the transducer by a screw mechanism (not shown). Container 13 (for example a container having a conical shape) has a tapered end 14 and holds within water, acoustic gel or any other substance that preferably has an impedance similar to that of the treated region, (for example a blood vessel). At end 14 there is a small opening 16. Focal point F is present inside the container 13. The arrangement of system 10 is such that the ultrasonic pressure wave (shown schematically as half circles extending from the focal, point), is administered to the blood vessel 17.

Figure 2A:
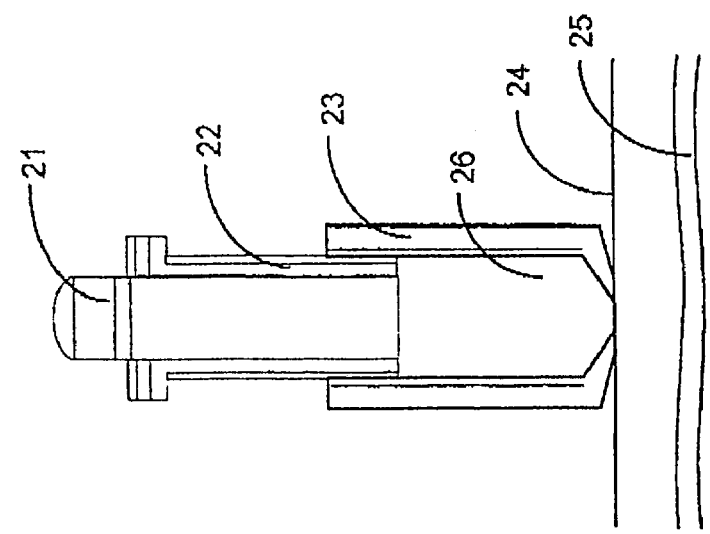
FIG. 2 shows a schematic representation of a method of the invention for closing a blood vessel.
Figure 2B:
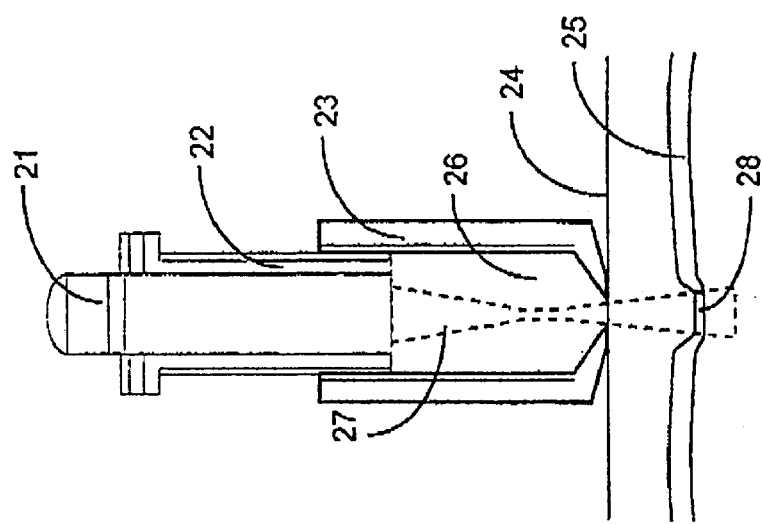
Figure 2C:
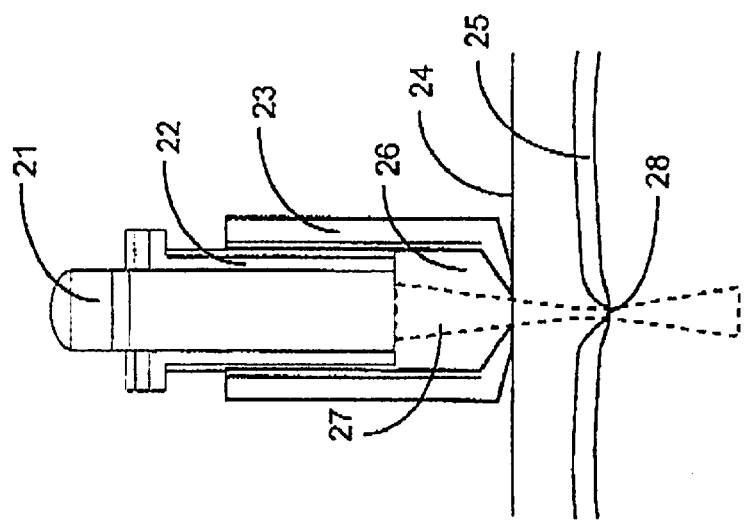

FIGS. 2A, 2B and 2C show schematically a system for closure of a blood vessel, according to the two step method of the invention, i.e. first application of an acoustic pressure wave, suitable for emptying the blood vessel from its contents, and second application of a focal ultrasonic beam, capable of thermal fusion of the blood vessels walls to each other.

The system 20 is composed of a focusing transducer 21 which is attached to a signal generator coupled to an amplifier and matching unit (the latter three not shown).

Transducer 21 is set in a holder 22 for ease of its manipulation, and both are threaded together into container 23 having the shape of a sleeve. The cavity of the container 26 is filled with acoustic coupling medium, such as degassed water, liquid. The system is placed on skin 24 above a blood vessel 25, which is to be closed. The first step of activation is shown in FIG. 2B. According to this step, holder 22 and attached transducer 21 are threaded as far as possible inside the container 23, so that focal point which is the narrowest part of beam 27, falls inside the acoustic coupling medium present in cavity 26. The acoustic wave passes through skin 24, and pushes against blood vessel 25, causing a construction of the blood vessel at side 28, which is directly under the wave's path 27 and in the direction of the wave's propagation. The parameters and position of the ultrasonic beam are such that the intensity and density of the beam energy are not sufficient to cause ablation of the blood vessel, but rather to push the liquid out of the radiation zone.

The second ultrasonic application is shown schematically in FIG. 2C.

At this step, and at a time period while blood does not still return to the constricted blood vessel, usually no more than a few seconds, the second ablating pulse is administered. Transducer 21 and holder 22, are moved, by threading action, down container 23, in order to bring transducer 21 closer to skin 24. As a result, the focal point, which is the narrowest point of ultrasonic wave 27, is not in cavity 26, but rather is focused directly at a depth of blood vessel 25, causing the area beneath the wave to completely close, and adhere to its other at site 28. This ablation is carried out while no liquid, or essentially no liquid, is present in the blood vessels and the vessels are still close to each other, due to the pressure caused in the previous step disclosed in FIG. 2B.

Figure 3A:
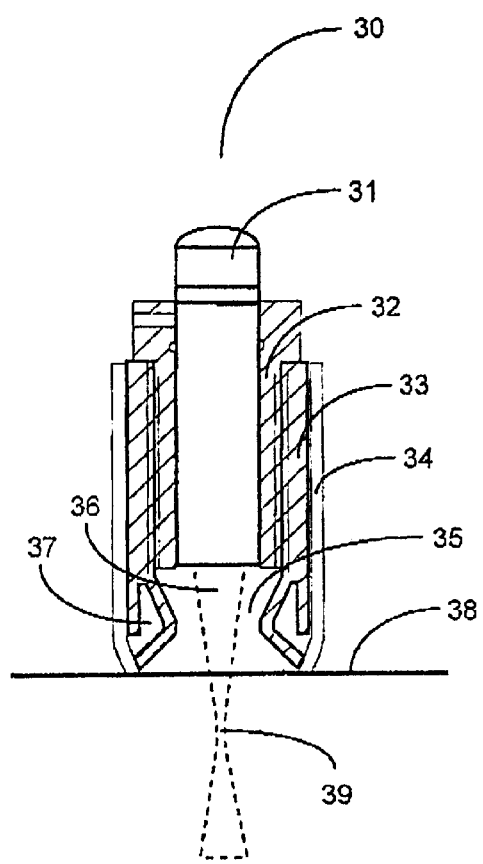
FIGS. 3A and 3B show another possibility for carrying out the method of the invention by use of a flexible outer sleeve.
Figure 3B:
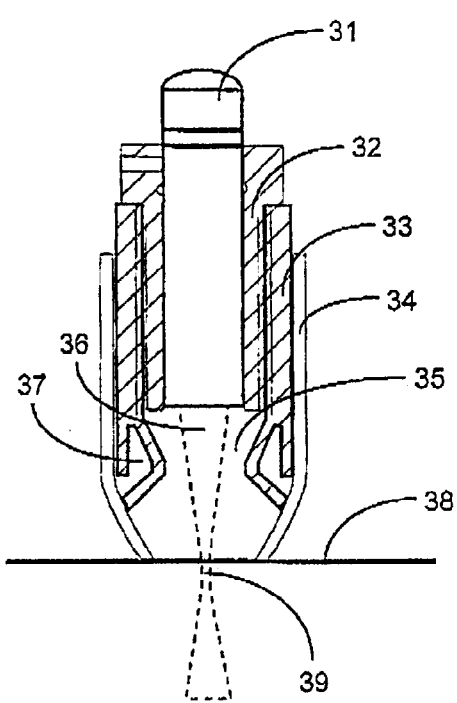

Reference is now made to FIGS. 3A and 3B which show another manner for carrying out closure of a blood vessel in accordance with the two-step method of the invention.

The system 30 comprises a transducer 31 set in its holder 32, and both the transducer and its holder are threaded into container 33. A flexible outer sleeve 34 covers container 33. The container's cavity 35 is filled with acoustic coupling medium such as gel or degassed water. Then, the system is placed on the skin at position 38. The distal end of container 33, in contact with the skin, has an air filled cavity 37 along its circumference. While air cavity 37 is not a requirement, it serves to isolate the ultrasonic wave at position 37 s from the hand of the person applying the system to the skin. When flexible outer sleeve 34 is retracted, the focal point 39 of ultrasonic wave 16 is created beneath the skin surface 38.

FIG. 3B shows another position of a system 30, where flexible sleeve 34 is moved forward and protracted. In this position, focal point 19 of ultrasonic wave 36 is moved up, and is in fact created inside container 33 in liquid media 35.

In accordance with the method of the invention, as a first step the position shown in FIG. 3B, is created, causing an acoustic pressure wave which pushes blood out of the vessel. Then, the outer flexible sleeve 34 is retracted, and the focal point thus moves outside of the container and beneath the skin onto the blood vessel, shown in FIG. 3A, causing its closure by thermal administration. The sleeve is retracted or protracted according to the width of the beam close to the skin.

Figure 4A:
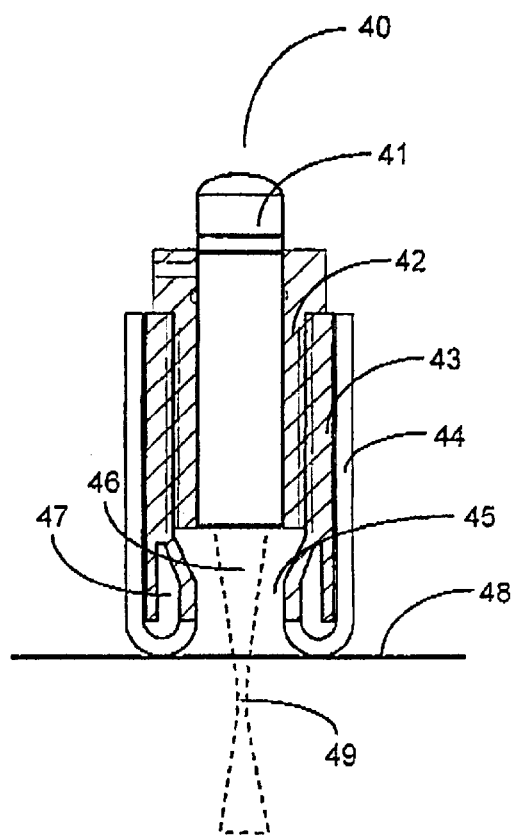
FIGS. 4A and 4B show yet another possibility for adjusting the distance between the transducer and the container.
Figure 4B:
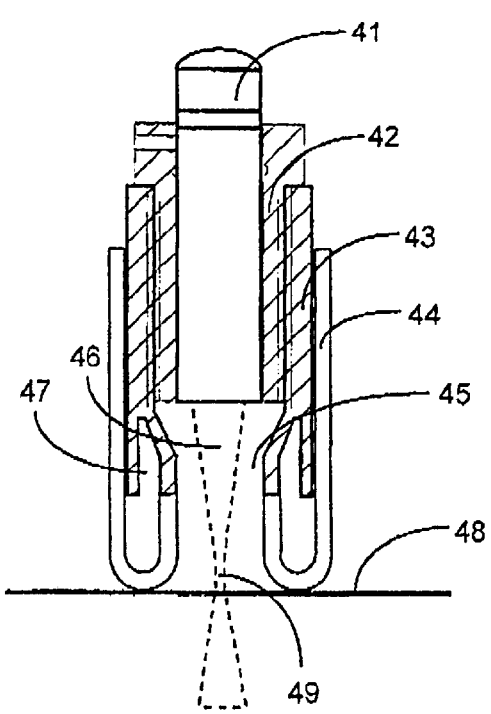

FIGS. 4A and 4B show another manner for adjusting the position of the focal point in accordance with the system of the invention 40. In FIG. 4A transducer 41 is set its holder 42 and together those are threaded into a container 43. A flexible outer sleeve 44 encloses a container 43. The container's cavity 45 is filled with acoustic coupling liquid such as acoustic gel or degassed water, and the system is placed on skin 48. At the end of the container 43 is an air filled cavity 47 around a circumference which serves to isolate, from ultrasonic irradiation, the band of the person holding the system next to the skin. The focal point 49, of ultrasonic wave 46 is created beneath the skin surface 48.

In order to relocate the focal point 49 to a position inside the container 43 (i.e. inside acoustic medium 45), flexible outer sleeve 44 is protracted inside container 43 by sliding it, for example, by a screw thread movements inside container 43. This causes the focal point of the ultrasonic wave 49 to move outward and into the container, and thus cause production of an ultrasonic acoustic wave which can produce acoustic pressure but is not sufficient to cause ablation beneath the skin 48.

Again, in accordance with the method of the invention, for carrying out the first step position of FIG. 4B is carried out, in order to cause an acoustic wave and push blood outside of the blood vessel and then the focal point is moved outside of the container, so it is placed directly on the blood vessel (not shown) as indicated in FIG. 4A, in order to cause its closure by the thermal effect of a focal ultrasonic beam.

EXAMPLE 1

An ultrasound system used for irradiation

A system as specified in FIG. 1 was used. The focus transducer 11 (IMASONIC, France) used was either 4.7 or 7.4 Mhz operated by function generator (HP 33120A, USA) and signal amplifier (Amplifier Research 75A250 USA). These components created intensities of up to 280 w/cm$^2$. The length of tie curved lens 12 and cone 13 together was 38 mm.

The cone was either attached to the lens so that the focal point was inside the container about 22 mm from the distal end of the container. This system was used to create an acoustic wave to push blood out of blood vessels.

EXAMPLE 2

Irradiation in a fish fin model

2–3 mm diameter zones with superficially observed red blood vessels at the fish tail fins were demarcated, and irradiated for 1–2 seconds with the system described in Example 1. Irradiation of different fish was carried out either under Condition A or Condition B. Under Condition A, the distal part of the cone was located 2 mm from the fin (in water) so as to mimic an effect on tissues located 2 mm deep from the skin surface, i.e. the water separating the distal end of the cone from the skin of the fish was used to mimic deep tissue and the chances viewed on the fish skin under these conditions were indicative of changes in deeper regions of the fish body that would have been observed if the system was indeed attached to the skin of the fish. Under Condition B, the distal part of the cone was attached to the fin and the whole irradiation was carried in two modes, either inside the water or outside of the water. This experiment was used to demonstrate irradiation on the immediate surface of the skin. The irradiation pulse used to empty the blood vessel was at a region 15 mm after the focal point. Immediately after application of the first "emptying" pulse the fin becamr pale as blood was pushed out of it. Than, immediately the second "ablating" pulse was applied to close the empty blood vessel.

The results of both treatments under conditions A and B were similar Macroscopically, during irradiation the blood was pushed away from the irradiated zone to adjacent zones of the irradiated capillaries, signifying in fact the effect of the acoustic wave in pushing blood out of a blood vessel. It was followed by collapse of the irradiated blood vessel or blood clotting at the interface between irradiated and normal zones of the blood vessel. Irradiated vessel remained pale and transparent and lacked blood perfusion. About 24 h later, the fin posterior to the irradiated vessel became necrotic, was disconnected, and fell apart. It must be noted that using the same device the ultrasonic wave was focused at deeper predetermined focal points in the muscles of the fish body, providing that no hard tissue, such as bone, was located in the beam's path.

EXAMPLE 3
Dual irradiation for fusion of blood vessels

Irradiation was carried out in order to fuse blood capillaries. The first irradiation was earned out using a container having a length larger than the focal point, so that the focal point was created insider the container (for example as in FIGS. 2B, 3B and 4B). This caused formation of an acoustic pressure that pushed the blood out of the irradiated vessels and forced the walls of the capillaries closer to each other.

Before blood perfusion returned to normal, the length of the container was changed to the configuration of FIGS. 2C, 3A and 4A, so that now the container's length was shorter than the lends of the focal point.

The second irradiation was performed so that the focal point formed outside of the container was on the capillary itself and caused thermal fusion of the capillary.

By utilizing the dual irradiation it was possible to decrease the amount of irradiation necessary for fusion of the capillary walls (the second irradiation), since the capillary was essentially empty of blood (which has a cooling effect) and its walls were closer to each other, as a result of the first irradiation.

Generally, the first irradiation (where the focal point is inside the container) is carried out for longer periods of lower intensities compared to the second irradiation (carried out where the focal point is outside the container) which is carried out for shorter periods of times at higher intensities.

What is claimed is:

1. An ultrasound system for the creation of an acoustic pressure wave for providing pressure on a desired location of an organ comprising:
   (I) at least one ultrasound generating element for producing a focused ultrasonic beam; and
   (II) at least one container having side walls and holding a liquid medium coupled at one end to the the ultrasound generating element for propagating the focused ultrasonic beam from the ultrasound generating element through a distal uncoupled end to the desired location of an organ, said container having a width such that the ultrasonic beam propagates therein without bouncing on the side walls of the container; and a length such that the focused ultrasonic beam's focal point is within the container.

2. A system according to claim 1, wherein the organ is selected from the group consisting of blood vessels, glands, ducts, tubes or vessels of the reproduction tract, nerves and muscles.

3. An ultrasound system, according to claim 1, wherein the at least one ultrasound generating, element comprises at least one transducer heaving a curved irradiation zone.

4. An ultrasound system according to claim 3, wherein the container has a conical shape with tapering side walls converging at the distal, uncoupled end.

5. An ultrasound system according to claim 3, wherein the distance between the ultrasound generating element and the distal part of the container is adjustable.

6. A system according to claim 5, wherein the transducer is slidably engagable inside an outer sleeve, which sleeve also holds container; said sleeve being in contact with the desired location of administration of the ultrasonic administration, and said distance is adjustable by sliding the transducer inside the sleeve.

7. An ultrasound system according to claim 1, wherein the ultrasound generating element comprises focusing means.

8. An ultrasound system according to claim 7, wherein the focusing means are acoustic lens.

9. An ultrasound system according to claim 8, wherein the container has a conical shape with tapering side walls converging at the distal, uncoupled end.

10. An ultrasound system according to claim 9, wherein the distal uncoupled end has an opening.

11. An ultrasound according to claim 9, wherein the distal uncoupled end is closed by material having impedance similar to that of the organ to which the beam is administered.

12. An ultrasound system according to claim 1 wherein the container has a conical shape and wherein the side walls are tapering side wall converging at the distal, uncoupled end.

13. An ultrasound according to claim 12, wherein the distal uncoupled end is closed by material having impedance similar to that of the desired location of the organ to which the focused ultrasonic beam is administered.

14. An ultrasound system according to claim 12, wherein the distance between the ultrasound generating element and the distal part of the container is adjustable.

15. A system according to claim 14, wherein the transducer is slidably engagable inside an outer sleeve, which sleeve also holds container; said sleeve being in contact with the desired location of administration of the ultrasonic administration, and said distance is adjustable by sliding the transducer inside the sleeve.

16. An ultrasound system according to claim 1, wherein the distal uncoupled end has an opening.

17. An ultrasound system according to claim 1, wherein the distance between the ultrasound generating element and the distal uncoupled of the container is adjustable.

18. A system according to claim 17, wherein the ultrasound generating element is slidably engageable inside an outer sleeve, which sleeve also holds the container; said sleeve adapted to be in contact with a desired location of administration, and said distance is adjustable by sliding the ultrasound generating element inside the sleeve.

19. A method for blocking a liquid containing vessel, at a desired portion thereof, in a treated subject, comprising the steps of:
   i) applying on the vessel at said desired portion a first ultrasonic pulse to produce an acoustic pressure wave having parameters sufficient for pushing liquid out of the vessel at said desired portion substantially without damaging the walls of the vessel; and
   iv) within a time period before liquid returns to the emptied portion of the vessel, applying a second ultrasonic pulse, being a focused ultrasonic wave with an acoustic focal point at a said desired portion, causing local elevation of temperature at said portion to adhere walls of the vessel at said portion with one another.

20. A method according to claim 19, wherein the liquid containing vessel is a blood vessel.

* * * * *